US008673290B2

(12) United States Patent
Jiang

(10) Patent No.: US 8,673,290 B2

(45) Date of Patent: Mar. 18, 2014

(54) **SPORULATION-DEFICIENT *B. TEXASPORUS* CELLS AND METHODS FOR EFFICIENT AND COST-EFFECTIVE INACTIVATION AND USE THEREOF**

(75) Inventor: Yiwei Jiang, Fort Worth, TX (US)

(73) Assignee: MYGALAXY Limited Company, Fort Worth, TX (US)

( * ) Notice: Subject to any disclaimer, the term of this patent is extended or adjusted under 35 U.S.C. 154(b) by 0 days.

(21) Appl. No.: 13/406,202

(22) Filed: Feb. 27, 2012

(65) Prior Publication Data

US 2012/0225037 A1 Sep. 6, 2012

Related U.S. Application Data

(60) Provisional application No. 61/447,703, filed on Mar. 1, 2011.

(51) Int. Cl.
*A01N 63/00* (2006.01)

(52) U.S. Cl.
USPC .......................................................... 424/93.1

(58) Field of Classification Search
None
See application file for complete search history.

(56) References Cited

U.S. PATENT DOCUMENTS

| | | | | |
|---|---|---|---|---|
| 4,302,544 | A | 11/1981 | Young et al. | |
| 4,450,235 | A | 5/1984 | Dean et al. | |
| 4,450,236 | A | 5/1984 | Dean et al. | |
| 4,465,773 | A | 8/1984 | Dean et al. | |
| 5,480,641 | A | 1/1996 | Casas-Perez | |
| 6,284,490 | B1 | 9/2001 | Frascotti et al. | |
| 7,498,404 | B2 * | 3/2009 | Jiang | 530/327 |
| 7,655,452 | B1 | 2/2010 | Hanagata et al. | |
| 2004/0247568 | A1 | 12/2004 | Guerino et al. | |

FOREIGN PATENT DOCUMENTS

WO WO 2005/074626 8/2005

OTHER PUBLICATIONS

Wu et al., Appl. Environ. Microbiol. 71(12): 8519-8530 (2005).*

He et al., "Inflammatory agonist stimulation and signal pathway of oxidative burst in neonatal chicken heterophils," *Comp Biochem Physiol A Mol Integr Physiol.*, 135(1):177-184, 2003.

Jiang et al., "The efficacy of TAMUS 2032 in preventing a natural outbreak of colibacillosis in broiler chickens in floor pens," *Poult Sci.*, 84(12):1857-1859, 2005.

Kogut et al., "Feeding the BT cationic peptides to chickens at hatch reduces cecal colonization by *Salmonella enterica* serovar *Enteritidis* and primes innate immune cell functional activity," *Foodborne Pathog Dis.*, 7(1):23-30, DOI: 10.1089/fpd.2009.0346, online 2009, print 2010.

Kogut et al., "The effects of the BT/TAMUS 2032 cationic peptides on innate immunity and susceptibility of young chickens to extraintestinal *Salmonella enterica* serovar *Enteritidis* infection," *Int Immunopharmacol.*, 7(7):912-919, 2007.

Lee et al., "*Bacillus subtilis* mutations that alter the pathway of phosphorylation of the anti-anti-sigmaF factor SpollAA lead to a Spo- phenotype," *Mol Microbiol.*, 40(1):9-19, 2001.

(Continued)

*Primary Examiner* — Patricia Leith
*Assistant Examiner* — Erin M Bowers
(74) *Attorney, Agent, or Firm* — Fish & Richardson P.C.

(57) ABSTRACT

Novel strains and methods for their use are provided. Particularly, foods and other oral products or treatments containing sporulation-deficient *Brevibacillus* strain when administered to a subject can inhibit or reduce the number of pathogens in the subject and improve the health of the subject.

23 Claims, 5 Drawing Sheets

(56) References Cited

OTHER PUBLICATIONS

Pomp et al., "Cell density dependent plating efficiency affects outcome and interpretation of colony forming assays," *Radiother. Oncol.*, 40:121-125, 1996.

Vijay-Kumar et al., "Metabolic syndrome and altered gut microbiota in mice lacking Toll-like receptor 5," *Science.*, 328(5975):228-231, Apr. 2010.

Wu et al., "Structure and biosynthesis of the BT peptide antibiotic from *Brevibacillus texasporus,*" *Appl Environ Microbiol.*, 71(12):8519-8530, 2005.

* cited by examiner

SPORULATION-DEFICIENT *B. TEXASPORUS* CELLS AND METHODS FOR EFFICIENT AND COST-EFFECTIVE INACTIVATION AND USE THEREOF

CROSS REFERENCE TO RELATED APPLICATIONS

This application claims the benefit of U.S. Provisional Application No. 61/447,703, filed Mar. 1, 2011, the entirety of which is incorporated by reference.

TECHNICAL FIELD

The present invention relates in general to the field of biotechnology, more specifically, to a stress-sensitive or sporulation-deficient strain of *Brevibacillus texasporus*, a method for efficient and cost-effective cell inactivation of the *B. texasporus* organism, and a feed or water additive derived from such strain.

BACKGROUND

Citation of any document herein is not an admission that the document is prior art, or considered material to patentability of any claim herein, and any statement regarding the content or date of any document is based on the information available to the application at the time of filing and does not constitute an affirmation or admission that the statement is correct.

Healthy animals or animals that are not infected by pathogenic organisms, such as pathogenic bacteria, grow faster and gain more weight per kilogram of feed. As a result, antimicrobial compounds have been used as growth promoters in farm animals since the 1940's. Typically, the antimicrobial compounds are administered in feed at a subtherapeutic or low dose.

While subtherapeutic doses of antimicrobial compounds have long been used to help farm animals maintain health and grow faster, recent reports demonstrate a link between the use of antibiotics and the presence of drug-resistant bacteria on the meat produced from these animals. As a result the European Commission, U.S. Department of Agriculture (USDA) as well as U.S. Food and Drug Administration (FDA) have all instituted bans and guidelines on the use of certain antibiotics as growth promoters. Currently, the regulations typically focus on the use of antibiotics that are the same as or similar to antibiotics used to treat humans. However, there is growing opposition in general to the use of all antibiotic drugs to enhance the growth of farm animals. Furthermore, the market for organically raised meat is increasing and to be certified organic, U.S. meat must come from animals raised without antibiotics. As a result there is a need for a new growth enhancer for farm animal feed.

In addition, companion animal health is a fast-growing market. Maintaining the health of companion animals (e.g., aging companion animals) via stimulation of innate immunity is an attractive approach to health maintenance in companion animals, and an orally delivered immune stimulant would be highly valued.

*Brevibacillus texasporus* (BT) (e.g., ATCC PTA-5854) is a recently identified soil bacterium that produces a group of cationic NRPS peptides (see, WO 2005/074626, Wu et al. 2005, and GenBank Accession No. AY953371). The cationic peptides from BT display a broad-spectrum of antibacterial activity in vitro, killing gram positive and negative bacteria, fungi and protozoa (WO 2005/074626). However, the high degree of 16S rDNA sequence identity (98.5%) between PTA-5854 and *Brevibacillus laterosporus*, a species defined almost exclusively by strains lacking the BT peptides, requires classification of *Brevibacillus texasporus* as a subspecies of *Brevibacillus laterosporus* (i.e., *Brevibacillus laterosporus* subsp. *texasporus*). Therefore, "*Brevibacillus texasporus*", "*Brevibacillus laterosporus* subsp. *texasporus*" and "*B. texasporus*" are synonymous and are used interchangeably when describing strains of the BT-peptide-producing subspecies.

Despite the in vitro antibacterial activity, the BT peptides seem to lack antibacterial activity in vivo. Vancomycin-resistant enterococci are highly sensitive to the BT peptides in vitro. However, the BT peptides at concentrations well above the minimal inhibition concentrations fail to decolonize commensal VRE from the mouse GI track.

However, an isolated peptide was shown to be effective in preventing colibacillosis and salmonellosis in chickens when used as a feed additive. In addition, this isolated peptide was also shown to be effective in promoting growth and increasing feed conversion in chickens.

Perhaps more importantly, the in vivo effect of the BT peptides appears to be independent of its in vitro antibiotic activities, as it is effective in preventing infections in chickens by *E. coli* and *Salmonella* at concentrations below its in vitro minimal inhibition concentrations (JIANG et al. 2005; KOGUT et al. 2007; KOGUT et al. 2010). It is also noted that blood heterophils and monocytes are primed for activation in chickens fed the BT peptides, pointing to innate immunostimulation as a likely mode of action. These features make the BT peptides an ideal feed additive and alternative to antibiotic compounds in farm animal production.

In addition, since innate immunity is now also known to play key roles in controlling viral and fungal infections as well as in preventing non-infectious diseases such as obesity/Metabolic Syndrome and type 2 diabetes mellitus (VIJAY-KUMAR et al. 2010), the BT innate immunity modulator should also have important applications in these therapeutic areas.

However, the economical value of the BT peptides as a feed additive is severely limited by the need to isolate the peptides, which increases the cost of production to a point where it is no longer economically viable. As an alternative to purifying the peptides, it is possible that the entire organism (PTA-5854), as discussed in international patent publication WO 2005/074626, could be used directly for the production of a feed additive.

Typically, a direct-fed microbial (DFM) or probiotic strain needs to reach the intestine in a viable form and in sufficient numbers, which requires the survival of the strain during feed processing and digestion (see, U.S. Pat. No. 5,480,641 and U.S. Patent Publication 20040247568). Since feed pellet production typically involves enough heat to significantly reduce viability, most probiotic strains are selected for their resistance to heat and the pH conditions found in the stomach. Currently the most stable probiotic strains are Bacillus spores, since bacterial spores are heat resistant and stay viable during long-term storage.

However, since the BT organism is not believed to be a symbiotic bacterium normally found in the intestinal track of farm animals, it is desirable and/or necessary to inactivate the organism before use. However, in spore producing strains this is problematic. In addition, at least one governmental regulatory authority considers the following criteria when assessing novel feeds involving microbial sources: safety of the production of the microorganism; safety of the microbial product to humans, animals and the environment; potential impact of horizontal gene transfer; interactions with gastrointestinal microflora; persistence in the gut; potential impact on humans and the environment due to shedding of viable microorganisms, particularly if there are perceived health impacts due to contamination of the meat (Directive on Guidelines for the Assessment of Novel Feeds: Microbial Sources, Draft—June 2007, The Canadian Food Inspection Agency). Therefore, when using microorganisms as a food additive there are two conflicting desired outcomes. The first is to maintain the organism in a viable condition throughout processing and digestion and the second diametrically opposed desire is to completely or nearly completely inactivate the organism without inactivation of the active peptides. An additional benefit of inactivation is that it removes or reduces the chances of horizontal gene transfer between *B. texasporus* and microorganisms in the gut and in the environment; eliminates or limits potential interactions with the gastrointestinal (GI) microflora; eliminates or reduces the potential risk on humans and the environment through shedding of viable cells; and/or eliminates or reduces contamination of the meat derived from the animal consuming the feed. Therefore, continuous spore formation by PTA-5854 severely limits the ability to use this strain as a DFM, since the spores are extremely resistant to most methods used to inactivate vegetative cells, mandating harsh and expensive methods for their removal.

As a result, there is a need in the art for a strain of *Brevibacillus texasporus* that can be used effectively as an inactivated DFM.

SUMMARY OF THE INVENTION

In one embodiment, the current invention is a feed or water additive that includes inactivated cells or an inactivated culture of a sporulation-deficient *B. texasporus* bacterial strain. The invention also relates to the use of inactivated dried cells or cultures (e.g., lyophilized or spray-dried cells or cultures) of the invention that may be added to a feed or drinking water for one or more animal, including, but not limited to, poultry, livestock, cattle, swine, chicken, horse, turkey, sheep, goat, duck, quail, Cornish game hen, pigeon, farm-raised fish, crabs, shrimp, fresh-water turtles, dog and cat. For example, cells of a culture of a sporulation-deficient *B. texasporus* strain may be inactivated via pasteurization, starvation, temperature (heat, cold or freezing), dehydration (e.g., heat-dry, freeze-dry, spray-dry, sun-dry, air-dry or vacuum-dry), acidification, akalination, alcohols, detergents, lysozyme, mechanical forces, quaternary ammonium cations, oxidizing agents (e.g. chlorine oxide, hydrogen peroxide, hypochlorite or ozone) and/or irradiation (e.g., UV, X-rays or gamma rays), the inactivated cells or culture then may be included in drinking water or an animal feed, such as a cereal-based feed, e.g., a feed containing at least one cereal selected from the group consisting of barley, soy, wheat, triticale, rye, maize and combinations thereof. In fact, the present invention may be added to a large variety of feeds. The inactivated cells of the invention or isolated peptides may be mixed with drinking water or a feed for livestock selected from the group consisting of a milk replacer, a grower feed, a finisher feed, a prestarter feed, a starter feed, water and combinations thereof.

The present invention also includes a method for increasing body weight gain and feed conversion in farm and companion animals, by inactivating (e.g., heat treatment or dehydration) sporulation-deficient *B. texasporus* cells or a cell culture and providing the inactivated sporulation-deficient *B. texasporus* cells or culture media plus cells to an animal in an amount sufficient to increase growth. Optionally, an effective amount of sporulation-deficient *B. texasporus* cells or a culture media containing the cells may be dried (dehydrated) and/or pelleted (a form of heat treatment) into an animal feed or added to drinking water.

Examples of feed ingredients also include cereal, soybean meal, isolated soybean protein, isolated soybean oil, isolated soybean fat, skimmed milk, fish meal, meat meal, bone meal, blood meal, blood plasma protein, whey, rice bran, wheat bran, and may further include a sweetener, a mineral, a vitamin, salt, and grass.

In an exemplary embodiment, sporulation-deficient *B. texasporus* cells are grown in a medium containing a suspension of feed ingredients (such as corn flour and soy flour). The culture may then be subject to cell inactivation and/or drying/dehydration to make a feed additive (wherein the particulates in the culture function as carriers for the BT peptides) or an enhanced feed.

The present invention also includes a method for preventing and/or treating microbial infections in animals, by providing inactivated sporulation-deficient *B. texasporus* cells or culture in an effective amount sufficient to treat and/or prevent microbial infections in the animal.

The present invention also includes a method for promoting weight gain and feed conversion in growing animals, by providing inactivated sporulation-deficient *B. texasporus* cells or culture in an effective amount sufficient to treat and/or prevent microbial infections in the animal.

The present invention also includes the use of sporulation-deficient cells as a human food or water additive.

In an exemplary embodiment, the invention provides sporulation-deficient strains of *B. texasporus* having survival rates less than about $3.5\times10^{-3}$, less than about $1\times10^{-4}$, less than about $1\times10^{-5}$, less than about $1\times10^{-6}$, less than about $1\times10^{-7}$, less than about $1\times10^{-8}$, or less than about $1\times10^{-9}$, which may be measured by subjecting a culture to a temperature of about 50° C. for about 5 minutes and determining the survival rate or colony forming ability.

In an exemplary embodiment, a sporulation-deficient *B. texasporus* strain also displays a decreased survival, such as a survival rate less than about $1\times10^{-9}$, when a culture is subjected to an inactivation treatment, such as starvation, freezing (in the absence of a effective amount of a cryoprotectant), dehydration (with a speed vacuum at 23° C.), pH extremes (e.g., pH 1.0 or pH 13.0), saturating butanol, addition of detergent (e.g., 1% SDS) or a lysing agent (e.g., lysozyme), sonication, mechanical force (e.g., a French press of animal feed pelleting machine) or hydrogen peroxide (e.g., greater than or equal to 1% $H_2O_2$).

The invention also relates to a method of increasing the BT peptide yield in a *B. texasporus* preparation by using cells derived from a sporulation-deficient *B. texasporus* strain. The present invention also relates to a method of increasing the stability and economic utility of the BT peptides in a *B. texasporus* preparation by using cells derived from a sporulation-deficient *B. texasporus* strain without purification or isolation of the BT peptides.

The invention also relates to a powdered form of *B. texasporus* cells, wherein the powder is substantially free of spores. In an exemplary embodiment, a culture of sporulation-deficient *B. texasporus* is grown in a liquid medium to a sufficient cell density and the culture is dehydrated or dried to produce a powder that is substantially free of spores. The powder may then be mixed with water or feed ingredients to produce an enhanced animal drink or food that does not contain a significant number of viable spores from the *B. texasporus* bacteria.

The invention also relates to a method of removing or decontaminating *B. texasporus* cells from the apparatus and/or facility used for *B. texasporus* production by treating the apparatus and/or facility to inactivate or kill the sporulation-deficient *B. texasporus* strain, thereafter the cells may simply be washed away. For example, steam or high temperature water may be used to clean the apparatus and/or facility, where the water would both remove the cells and kill them (due to the temperature), thereby effectively removing the *B. texasporus* cells from the apparatus and/or facility.

The invention also relates to a method of stimulating the immune system in an animal or human, by administering an effective amount of a sporulation-deficient *B. texasporus* strain. For example, a sporulation-deficient *B. texasporus* strain may be grown, the cells may be harvested, with or without the culture media, and the cells may be admixed with water or additional food ingredients to produce an enhanced drink or food that stimulates the immune system of the animal that it is administered to. For example, a sporulation-deficient *B. texasporus* strain may be inactivated and directly fed to an animal or human to stimulate the immune system of the animal or human. In another exemplary embodiment, the invention relates to an enhanced food that stimulates the immune system of an animal or human by administering an effective amount of a sporulation-deficient *B. texasporus* strain and a food carrier to the animal or human.

A sporulation-deficient *B. texasporus* strain may be grown and admixed with water or food ingredients to produce an enhanced drink or food that stimulates the immune system, for example, it may boost the immune response to a vaccine that is administered to the animal or human either in combination with the enhanced drink or food or subsequent to delivering the enhanced drink or food. In addition, a sporulation-deficient *B. texasporus* strain may be inactivated and fed to an animal or human, for example the inactivated cells may be dried, shipped to a desired processing and/or administration site and admixed with water or food that is to be consumed by an animal or human, wherein the food or water does not contain viable spores from the *B. texasporus* strain.

The present invention also relates to a composition for stimulating the immune system of an animal, including a human, by administering an effective amount of a sporulation-deficient *B. texasporus* strain in combination with one or more vaccines. For example, a sporulation-deficient strain may be grown, the cells harvested (with or without the culture media, e.g., the cells may be washed after centrifugation), and administered to an animal either prior to or in combination with a vaccine, wherein the cells prime or boost the immune system's response to the vaccine.

The present invention also relates to a composition and/or method of preventing and/or treating a disease in an animal, comprising administering a sporulation-deficient *B. texasporus* strain to an animal. For example, the treatment may involve reducing a pathogenic microbial population in an animal. Exemplary pathogens that may be reduced include, but are not limited to, *Acinetobacter, Bacilli, Borrelia, Campylobacter, Clostridia, E. coli, Enterococcus*, Foot-and-mouth disease virus, *Gonorrhea, Haemophilus*, Influenza virus, *Mannheimia, Mycobacteria, Mycoplasma, Pasteurella, Pseudomonas, Salmonella, Staphylococcus* and *Streptococcus*. Exemplary diseases include, but are not limited to, colibacillosis, salmonellosis, necrotic enteritis, coccidiosis, influenza, foot-and-mouth disease, porcine reproductive & respiratory syndrome, bovine shipping fever pneumonia, urinary track infection, obesity/Metabolic Syndrome and type 2 diabetes mellitus.

Sporulation-deficient *B. texasporus* strains, designated as PTA-12307 (Strain MYG113), PTA-12308 (Strain MYG110), PTA-12309 (Strain MYG107) and PTA-12310 (Strain MYG11) were deposited on Dec. 7, 2011. All of these strains have been deposited under the provisions of the Budapest Treaty, with the American Type Culture Collection (ATCC), 10801 University Blvd., Manassas, Va. 20110-2209, USA) and incorporated by reference.

The present invention also relates to at least one bacterial strain belonging to the genus *Brevibacillus* selected from the group consisting of at least one of PTA-12307, PTA-12308, PTA-12309 and PTA-12310.

One approach that can be used to inactivate the cells of the invention involves growing the cells in an appropriate medium, then adding feed ingredients to the culture or the culture to the feed ingredients to dehydrate the cells.

Another approach (beside heat shock) that can be used to inactivate the cells of the invention involves subjecting the cells to a pH extreme, such as a pH of about 1, about 2, about 3, about 4, about 5, about 9, about 10, about 11, about 12, about 13, or about 14.

Changes in pH sufficient to inactivate the cells of the invention can be accomplished by addition of a base, acid and/or other composition to effectively shift the pH beyond a physiologically tolerated range. For example, carbon dioxide can dissolve in water to produce carbonic acid and lower the pH to cause inactivation of the cells.

Another approach that can be used to inactivate cells of the invention is high pressure processing (also known as "high pressure treatment" or "ultra-high pressure treatment" or "ultra-high pressure sterilization"), which is a process that may involve the application of pressures in the range of 100-1,000 MPa (14,500-145,000 psi), or 150-600 MPa (25,000 to 90,000 psi) to eliminate vegetative cells of bacteria, mould and the like from products where these cells exist.

An example of a high pressure treatment is the French press approach (French pressing), which disrupts cell by applying a pressure to a cell suspension (up to 40,000 psi) and then suddenly releasing the pressure. Thus, the sporulation-deficient strain of the invention may be inactivated by the application and release of a pressure of about 40,000 psi, 20,000, 10,000, 5,000, 2,000, 1,000 psi, and any combination thereof.

Yet another approach that can be used to inactivate the cells of the invention involves subjecting the cells to an alcohol at a final concentration of about 70%, about 60%, about 50%, about 40%, about 30%, about 20%, about 10%, about 5%, about 2%, or about 1% (v/v).

Yet another approach that can be used to inactivate the cells of the invention involves subjecting the cells to a detergent at a final concentration of about 10%, about 5%, about 2%, about 1%, about 0.5%, about 0.2%, or about 0.1% (w/v).

Yet another approach that can be used to inactivate the cells of the invention involves subjecting the cells to dehydration by reducing the water content in the environment surrounding *B. texasporus* cells to a level below about 80%, about 70%, about 60%, about 50%, about 45%, about 40%, about 35%, about 30%, about 25%, about 20%, about 15%, about 10%, about 5%, about 2% or about 1%.

In an exemplary embodiment, a culture of sporulation-deficient cells according to the invention are prepared, treated by one or more inactivation methods, and applied to an animal feed. For example, a culture of sporulation-deficient cells may be grown using a high yield system and then spray dried to produce a powder. In this scenario, spray drying is used to inactivate the cells and produce a product that may then be added to dried feed stocks. Alternatively, the cell culture may be inactivated by addition of heat and/or pressure, such as during the process of preparing pelletized feed.

In another exemplary embodiment, a culture of sporulation-deficient cells according to the invention, such as MYG107, MYG110, or MYG113, are grown in a liquid medium and then added to a substantially dry mixture of animal feed ingredients or to animal feed grain to produce a mixture having a final moisture content between about 10% and about 25% (relative to the solids), the moistened mixture is then run through a pellet mill to produce pellets of the appropriate size, which are then dried to a final moisture content, for example, about 5%. In this example, addition of the cells to the substantially dry mixture of animal feed ingredients provides a form of dehydration that is then accentuated by addition of heat and the drying of the pellets. Under these conditions it is believed that all or virtually all of the cells will be inactivated.

In another exemplary embodiment, feed ingredients, including #2 yellow corn, soy meal, rice hulls, rendered protein products, salt, powdered limestone phosphate, liquid animal fat, and liquid choline are used to produce a feed containing inactivated cells of the invention. A batch of feed is generally prepared by mixing the dry powdered or ground ingredients into a homogenous state and then adding the liquid ingredients, which may include a sporulation-deficient culture of *B. texasporus* cells (a form of dehydration). The moistened mixture is conveyed to a conditioning chamber, where steam is added (providing a form of heat shock) and the feed becomes a mash. This mash is mixed thoroughly before pelleting and entry into the pellet mill. In the pellet mill, the soft hot mash is forced through a die and formed into cylinder shaped pellets. The pellets are sent to a cooler/dryer, where a fan pulls ambient air through the bed of pellets to remove moisture (further dehydrate) and heat from the pellets. A conveyor and bucket elevator may then be used to move the feed to a liquid coating process, where animal fat is sprayed on the feed at about 2% by weight. The finished feed is then ready for use.

In another exemplary embodiment, about $1.0\times10^{10}$, $1.0\times10^{11}$, $1.0\times10^{12}$, $1.0\times10^{13}$, $1.0\times10^{14}$, or $1.0\times10^{15}$ inactivated cells of a sporulation-deficient *B. texasporus* strain are added to about 1000 kg of animal feed.

In yet another exemplary embodiment, an effective dose of sporulation-deficient *B. texasporus* cells are administered to an animal. In yet another exemplary embodiment, an effective in-water or in-feed dose of sporulation-deficient *B. texasporus* cells comprises BT peptides between about 5 ppm and about 1000 ppm, between about 15 ppm and about 1000 ppm, between about 20 ppm and about 1000 ppm, between about 5 ppm and about 100 ppm, between about 10 ppm and about 100 ppm, between about 20 ppm and about 100 ppm, between about 5 ppm and about 75 ppm, between about 10 ppm and about 75 ppm, between about 20 ppm and about 75 ppm, between about 5 ppm and about 50 ppm, between about 10 ppm and about 50 ppm or between about 20 ppm and about 50 ppm.

In another exemplary embodiment, dehydration of a sporulation-deficient *B. texasporus* strain of the invention is performed by; freeze drying, vacuum drying, spray drying, osmotic dehydration, fluidized bed dehydration, solvent evaporation dehydration, sonication assisted dehydration, microwave-assisted dehydration, RF-assisted dehydration, and/or combinations thereof.

In another exemplary embodiment, dehydration of the sporulation-deficient *B. texasporus* cells or culture is done by addition of a water-absorbing substance (e.g., a feed ingredient), heat (such as generated in a animal feed pelleting process) and/or evaporation.

DETAILED DESCRIPTION OF THE INVENTION

Figure 1:
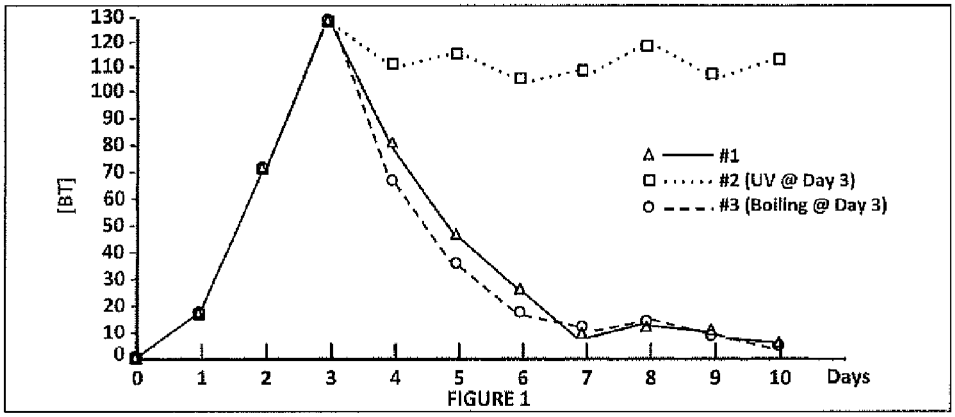
FIG. 1 illustrates consumption of the BT peptides by spores of PTA-5854. PTA-5854 was inoculated into LB and grown in a 37° C. air shaker. Samples were taken every day and the BT peptides were extracted and assayed for activities. One artificial unit is 0.8 ug/ml of BT peptides. On Day 3, the culture was split into three aliquots (#1, #2 and #3). Aliquot #1 was untreated. Aliquot #2 was UV-irradiated in a UV cross-linker for 10 minutes. Aliquot #3 was boiled for 10 minutes. The aliquots were then incubated in the 37° C. air shaker.

As used herein and in the appended claims, the singular forms, for example, "a", "an", and "the," include the plural, unless the context clearly dictates otherwise. For example, reference to "a *B. texasporus* bacteria" includes a plurality of such bacteria, and reference to a "cell" is also a reference to a plurality of similar cells, and equivalents thereof.

As used herein, "about" means reasonably close to, approximately, or a little more or less than, the stated number or amount.

As used herein, "animal" means any invertebrate or vertebrate, including horses, goats, sheep, cattle, swine, chickens, turkeys, game hens, geese, ducks, dogs, cats, parrots, fish, crabs, shrimp, fresh-water turtles, humans and the like.

As used herein, "feed" or "food" means any substance or mixture of substances containing amino acids, anti-oxidants, carbohydrates, condiments, enzymes, fats, minerals, non-protein nitrogen products, proteins, vitamins, and/or binders and may contain pelletizing, coloring, foaming and/or flavoring agents, manufactured, sold or presented for consumption by animals, such as livestock and domestic animals, or a human, to provide at least a part of the nutritional requirements of the animal or human, and/or for the purpose of preventing or treating nutritional disorders in the animal. As a vital nutrient, water is considered a feed ingredient and an aqueous drink is a feed or food.

As used herein, "inactivate" or "inactivation" means any treatment or stress, such as starvation, temperature shock, dehydration/lyophilization/drying (e.g., heat-drying, freeze-drying, spray-drying, sun-drying, air-drying and/or vacuum-drying), pH changes (e.g., acidification or alkalination), alcohol treatment, treatment with a detergent, filtration, treatment with metals such as silver and zinc, pressure treatment such as high pressure processing, enzymatic disruption (e.g., treatment with lysozyme), mechanical force (e.g., sonication), treatment with quaternary ammonium cations, oxidizing agents (e.g., chlorine oxide, hydrogen peroxide, hypochlorite and/or ozone), salinization, electrical field treatment, microwave treatment, electron beam treatment, irradiation and/or combinations thereof, that is generally unable to kill spores and that reduces the relative colony forming efficiency (survival rate) of a culture to less than about $1\times10^{-3}$, less than about $1\times10^{-4}$, less than about $1\times10^{-5}$, less than about $1\times10^{-6}$, less than about $1\times10^{-7}$, less than about $1\times10^{-8}$, or less than about $1\times10^{-9}$.

As used herein, "inactivated cells or culture" of a sporulation-deficient *B. texasporus* strain means a mixture of non-viable *B. texasporus* cells, at least partially released cellular content and/or culture medium ingredients. It should be noted that inactivation of a sporulation-deficient strain of the invention may result in the lysis of many, most or all of the cells, depending on the inactivation conditions used. Therefore, an "inactivated cell," "inactivated culture" and equivalent phrases, includes within their meaning a cell lysate produced, at least in part, by the inactivation process.

As used herein, "mutation" means any change in the sequence of a nucleic acid, including insertions, deletions, transitions and transvertions of one or more nucleotides. The size of the deletion or insertion can vary from a single nucleotide to many genes.

As used herein, "phenotype" means the observed biochemical, physiological, and/or morphological characteristics of a cell or culture of cells.

As used herein, "sporulation-deficient" refers to a bacterial strain that exhibits any detectable defect in the spore formation process or product as compared to the fully sporulation-competent, wild-type (wt) counterpart strain. The term "sporulation-deficient" thus refers to any strain having a sensitivity to a stress such as starvation, temperature shock, dehydration, acidification, alkalination, alcohols, detergents, lysozyme, mechanical forces, quaternary ammonium cations, oxidizing agents and/or irradiation that reduces the relative colony forming efficiency (survival rate) of a culture to less than about $8.1\times10^{-7}$, less than about $3.5\times10^{-3}$, less than about $1\times10^{-4}$, less than about $1\times10^{-5}$, less than about $1\times10^{-6}$, less than about $1\times10^{-7}$, less than about $1\times10^{-8}$, or less than about $1\times10^{-9}$, which includes sporulation-incompetent and substantially sporulation-impaired cells, or phrased another way, cells wherein spores are not formed because the strain is not capable, or the cells have a diminished capability of forming spores or cells wherein spores are formed, but the spores may not be viable or the spores are sensitive to an inactivation stress and rendered nonviable upon exposure thereto. Sporulation-deficiencies may be measured by any of the methods described herein, for example, an actively growing culture may be subject to a heat shock of about 50° C. or about 70° C. for about five minutes and the relative colony forming efficiency measured against an untreated culture or aliquot of the culture that has not been subject to heat shock.

"Starvation" is a nutrient deprivation that causes a reduction in the number of active or vegetative cells (and stimulates spore formation and/or cell death). Wild-type *B. texasporus* cells undergo sporulation at least in part to survive starvation, but sporulation-deficient *B. texasporus* cells cannot avoid cell death caused by starvation. Thus, an inactivated culture of a sporulation-deficient *B. texasporus* strain may be simply obtained by inoculating the strain into a growth medium and incubating the strain for an extended period of time such that the cells die of starvation after the initial growth phase.

As used herein "temperature shock" means a heat of about 50° C. to about 100° C., cold of about 0° C. to about 16° C. or freezing.

"Dehydration" is defined as any process or treatment leading to a reduction of the water content in the environment surrounding *B. texasporus* cells, osmotic shock, for example, reducing the water content in the surrounding environment to a level below about 80%, about 70%, about 60%, about 50%, about 45%, about 40%, about 35%, about 30%, about 25%, about 20%, about 15%, about 10%, about 5%, about 2% or about 1%.

An effective amount of the cells of the invention is preferably determined by a physician or veterinarian based on the factors such as the animal's size, age, weight and/or medical condition.

Spore formation in PTA-5854 limits the yield level of the BT peptides, since PTA-5854 spores appear to degrade the BT peptides. Without wishing to be bound by theory, it appears that spore formation and/or spore activation reduces the production of the BT peptides by PTA-5854. As shown in FIG. 1, continued culture of PTA-5854 in LB culture beyond Day 3 at 37° C., at which time nutrient depletion has at least begun, resulted in a depletion of the BT peptides (#1). This BT peptide depletion could be prevented by UV-irradiation at Day 3, which killed both active (vegetative) cells and spores (#2). However, the BT depletion could not be prevented by boiling at Day 3, which only killed the active cells but did not inactivate the spores (#3).

In addition to the reduction in BT peptide levels, spore formation in PTA-5854 prevents the most economical method of using the strain as a feed additive. In particular, the use of the BT peptides as a feed additive requires a low production cost, which practically rules out any peptide purification steps. As a result, the most economical BT-based feed additive would be a dehydrated *B. texasporus* culture. Dehydration can only inactivate vegetative cells but not the spores of *B. texasporus*, therefore, dehydration cannot inactivate a sporulation proficient strain. Furthermore, the spores from such a strain can germinate and deplete surrounding BT peptides, where degradation of the BT peptides by the germinating spores would also pose a serious problem for the stability of any feed product.

Finally, a feed additive containing *B. texasporus* spores may not meet regulatory standards and causes concerns regarding spreading the producer strain. As a result it is highly desirable to be able to effectively inactivate or eliminate spores.

However, *B. texasporus* continuously forms spores that are difficult to eliminate or inactivate. Common techniques that could be used to inactivate *B. texasporus* and the resulting spores include, gamma irradiation, autoclaving and other extreme treatments. Although gamma irradiation is effective in eliminating spores without damaging the BT peptides in particular physical settings, it is generally considered neither practical nor cost-effective by industry. Autoclaving is another effective method to eliminate spores, but the process damages the BT peptides, thus rendering this method undesirable.

The most practical and cost-effective method of cell inactivation in an industrial setting is a brief treatment of moderate heat (such as Pasteurization, e.g., 70° C. for 30 minutes) and/or dehydration, which the BT peptides can withstand. Since *B. texasporus* spores are quite resistant to heat treatment (the spores can withstand significant stress levels, such as boiling at 100° C. for 60 minutes, Table 1, and dehydration, Table 2), a sporulation-deficient strain sensitive to moderate temperature and/or dehydration is needed for the practical and/or cost-effective use of *B. texasporus*, such as for a DFM. The present invention provides a sporulation-deficient *B. texasporus* strain that can be inactivated using BT peptide-safe techniques, such as pasteurization, pelletization, lyophilization and/or drying, wherein the inactivation conditions are capable of inactivating vegetative cells, but generally not wild-type spores.

Examples of techniques useful for inactivation of vegetative cells include, but are not limited to, starvation, temperature shock (heat such as pasteurization or cold such as freezing), dehydration/lyophilization/drying (e.g., heat-drying, freeze-drying, spray-drying, sun-drying, air-drying and/or vacuum-drying), pH changes (e.g., acidification or alkalination), alcohol treatment, treatment with a detergent, filtration, treatment with metals such as silver and zinc, pressure treatment such as high pressure processing, enzymatic disruption (e.g., treatment with lysozyme), mechanical force (e.g., sonication), treatment with quaternary ammonium cations, oxidizing agents (e.g., chlorine oxide, hydrogen peroxide, hypochlorite and/or ozone), salinization, (pulse) electrical field treatment using radio frequency (RF) energy, microwave treatment, electron beam treatment, irradiation (e.g. UV, X-rays or gamma rays) and combinations thereof. In an exemplary embodiment one or more of these techniques may be used to inactivate sporulation-deficient cells of the invention.

According to the inventor's best knowledge, there is no publication documenting a sporulation deficiency meeting the perceived regulatory standard for an inactivated DFM at a stress survival rate of $<10^{-6}$, $<10^{-7}$, $<10^{-8}$, or $<10^{-9}$. For example, in academic publications, a bacillus stress survival rate at $10^{-2}$ is called sporulation-deficient (LEE et. al., 2001); whereas methods published in issued U.S. Pat. Nos. 4,302,544, 4,450,235, 4,450,236, 4,465,773, 6,284,490 and 7,655,452 could only produce sporulation-deficient ("asporugenous" or "asporugenic") bacillus strains with a stress survival rate on the order of $10^{-7}$. Therefore, the art to produce bacillus strains with a sporulation deficiency at a stress survival rate of $<10^{-9}$ seemed to be lacking The need to create such art was great considering the fact that the more potent gene deletion method is not a suitable choice (and the only usable method of mutagenesis is a chemical one which mostly causes silent or "leaky" point mutations) for two reasons. First, *B. texasporus* is a non-genetically tractable organism and a gene deletion cannot be performed. Second, a resultant gene knockout strain would be a genetically modified organism (GMO) which is prohibited in human food in regions such as European Union. In another exemplary embodiment, the inactivation method is sufficient to reduce the survival rate of a sporulation-deficient strain according to the invention to less than about $1\times10^{-4}$, less than about $1\times10^{-5}$, less than about $1\times10^{-6}$, less than about $1\times10^{-7}$, less than about $1\times10^{-8}$, or less than about $1\times10^{-9}$, but wherein the inactivation method is insufficient to reduce the survival rate of sporulation-competent PTA-5854 below about $3.3\times10^{-1}$ or below about $4.3\times10^{-1}$.

Example 1

An attempt to isolate a sporulation-deficient mutant of PTA-5854 was made as follows. PTA-5854 cells were mutagenized with EMS and then plated onto LB-agar. About 50,000 colonies were screened for sensitivity to treatment at 75° C. for 1 hour, and 42 temperature sensitive candidate strains were isolated. These initial candidate strains were colony-purified and retested for heat sensitivity. The PTA-5854 strain and the temperature sensitive candidate strains were grown in liquid LB medium at 37° C. for three days. The cells were then dispensed into sterile microfuge tubes as 100 μl aliquots and incubated at various temperatures (75, 70, 65, 60, 55, 50 or 37° C.) for different lengths of time (5, 15, 30 or 60 minutes). The treated cells were plated onto LB-agar and incubated at 37° C. overnight to determine plating efficiency. The survival rate after a heat shock treatment was calculated as the plating efficiency after heat shock divided by the plating efficiency at 37° C. without heat shock.

Of the initial 42 isolates, several temperature sensitive mutants were confirmed. The strain B7 showed the best temperature sensitive phenotype (Table 1). A brief 5-minute treatment at 50° C. resulted in a survival rate of $8.1\times10^{-7}$ (about $1\times10^{-6}$), and higher temperatures and longer incubations did not decrease the survival rate significantly. This level of cell inactivation is considered inadequate for purpose of using *B. texasporus* as a DFM. Repeated mutagenesis and mutant isolations of PTA-5854 did not produce a strain having a better temperature sensitive phenotype than B7. It was reasoned that more than one mutation might be necessary for a tighter temperature sensitive phenotype to allow more efficient cell inactivation. However, mutagenesis of B7 did not yield mutants with an improved temperature sensitive phenotype, possibly due to the poor health of B7 (relative to the parental PTA-5854).

TABLE 1

Temperature sensitivities of *B. texasporus* cells (as two-day old L-Broth cultures)

| | | Temperature sensitivity | | |
|---|---|---|---|---|
| Strain | Genotype | Temperature (° C.) | Duration (min) | Survival Rate |
| PTA-5854 | Spo+++ | 100 | 60 | $3.3\times10^{-1}$ |
| PTA-5854 | Spo+++ | 75 | 60 | $4.3\times10^{-1}$ |
| B7 | Spo− | 50 | 5 | $8.1\times10^{-7}$ |
| B7 | Spo− | 75 | 5 | $1.2\times10^{-6}$ |

TABLE 1-continued

Temperature sensitivities of *B. texasporus* cells (as two-day old L-Broth cultures)

| Strain | Genotype | Temperature sensitivity: Temperature (° C.) | Duration (min) | Survival Rate |
|---|---|---|---|---|
| MYG11 (PTA-12310) | Spo+/− | 50 | 5 | $3.5 \times 10^{-3}$ |
| MYG11 (PTA-12310) | Spo+/− | 75 | 5 | $3.7 \times 10^{-3}$ |
| MYG107 (PTA-12309) | Spo−−− | 50 | 5 | $<10^{-9}$ |
| MYG110 (PTA-12308) | Spo−−− | 50 | 5 | $<10^{-9}$ |
| MYG113 (PTA-12307) | Spo−−− | 50 | 5 | $<10^{-9}$ |

A new bacterial strain (MYG11, accession number PTA-12310) was isolated from a soil sample. S16 rDNA sequencing of this strain shows that it is of the same species as PTA-5854, but possesses a significantly different phenotype with regard to heat treatment. MYG11 grows rapidly in L-Broth media at 37° C. and it shows an initial sensitivity to high temperature, or a sporulation-deficiency. A treatment at 50° C. for 5 minutes resulted in a survival rate of $3.5\times10^{-3}$ (Table 1). Therefore, MYG11 was mutagenized and about 50,000 colonies were screened for mutants displaying increased temperature sensitivity. At least three mutants, MYG107 (accession number PTA-12309), MYG110 (accession number PTA-12308) and MYG113 (accession number PTA-12307), were isolated by this method and found to show severe sporulation-deficiencies. In sharp contrast to PTA-5854 and B7, treatment at a temperature of 50° C. for 5 minutes resulted in survival rates for MYG107, MYG110 and MYG113 lower than $10^{-9}$. Thus, the invention provides for *B. texasporus* strains that have a survival rate lower than about $10^{-8}$ or about $10^{-9}$ when exposed to a temperature of at least 50° C. for at least 5 minutes.

MYG107 has a doubling time of about 45 minutes in a log-phase L-Broth culture and was further characterized. Given that the survival rate of MYG107, MYG110 and MYG113 are at or below the detectable limit of the cultures used in this experiment, it is believed that MYG107, MYG110 and MYG113 have a fundamental defect in sporulation, are highly sporulation-deficient strains, which is further supported by the fact that the BT yield from MYG107 is believed to be more than tripled in comparison to PTA-5854.

Moreover, typical lateral endospores are detectable in a culture of PTA-5854 at nearly all stages. Such lateral endospores have not been observed in cultures of MYG107 at any stage, supporting the notion that MYG107 has a fundamental defect in sporulation. Furthermore, MYG107 displays sensitivities to other types of stress that inactivate vegetative cells but not spores (Table 2).

TABLE 2

Stress sensitivities of *B. texasporus* cells (as two-day old L-Broth cultures)

| Stress | Strain | Survival Rate |
|---|---|---|
| Freezing (−20° C. for 1 h) | PTA-5854 | $4.2 \times 10^{-1}$ |
| | MYG107 | $<10^{-9}$ |
| pH 1.0 (transient, at room temperature) | PTA-5854 | $4.5 \times 10^{-1}$ |
| | MYG107 | $<10^{-9}$ |
| pH 13.0 (transient, at room temperature) | PTA-5854 | $5.1 \times 10^{-1}$ |
| | MYG107 | $<10^{-9}$ |
| 1% Butanol (transient, at room temperature) | PTA-5854 | $5.6 \times 10^{-1}$ |
| | MYG107 | $<10^{-9}$ |
| 1% SDS (transient, at room temperature) | PTA-5854 | $3.3 \times 10^{-1}$ |
| | MYG107 | $<10^{-9}$ |

TABLE 2-continued

Stress sensitivities of *B. texasporus* cells (as two-day old L-Broth cultures)

| Stress | Strain | Survival Rate |
|---|---|---|
| 1% hydrogen peroxide (transient, at room temperature) | PTA-5854 | $3.3 \times 10^{-1}$ |
| | MYG107 | $<10^{-9}$ |
| Lysozyme (1 mg/ml at 37° C. for 1 h) | PTA-5854 | $7.2 \times 10^{-1}$ |
| | MYG107 | $<10^{-9}$ |
| French pressuring (three times, at room temperature) | PTA-5854 | $1.5 \times 10^{-1}$ |
| | MYG107 | $<10^{-9}$ |
| Starvation (for 7 days at 37° C.) | PTA-5854 | $3.3 \times 10^{-3}$ |
| | MYG107 | $<10^{-9}$ |
| Dehydration (in speed vacuum at 23° C. for 1 h) | PTA-5854 | $3.9 \times 10^{-1}$ |
| | MYG107 | $<10^{-9}$ |

In a freezing sensitivity test, the wild-type PTA-5854 strain and MYG107 were grown in liquid LB medium at 37° C. for two days, and the cells were then dispensed into sterile microfuge tubes as 100 μl aliquots and incubated at −20° C. for 60 minutes (or upon formation of ice). The freeze-treated and untreated cells were plated onto LB-agar and incubated at 37° C. overnight to determine plating efficiency. The survival rate for freezing was calculated (the plating efficiency for treated cells/the plating efficiency of untreated cells). Freezing resulted in a survival rate about less than $10^{-9}$ for MYG107 in comparison to the survival rate of PTA-5854 at about $4.2\times10^{-1}$.

In an acidification sensitivity test, the wild-type PTA-5854 strain and MYG107 were grown in liquid LB medium at 37° C. for two days, and the cells were then dispensed into sterile microfuge tubes as 100 μl aliquots. The pH was adjusted to about 1.0 (at room temperature) by adding 10 μl of 1 M HCl to each aliquot and then immediately neutralized by adding 10 μl of 1 M NaOH. The acid-treated and untreated cells were plated onto LB-agar and incubated at 37° C. overnight to determine plating efficiency. The acidification resulted in a survival rate about less than $10^{-9}$ for MYG107 in comparison to a survival rate of PTA-5854 at about $4.5\times10^{-1}$.

An alkalination sensitivity test was performed in a similar fashion except that NaOH was first added to adjust pH to 13.0 then HCl was added for neutralization. The alkalination resulted in a survival rate about less than $10^{-9}$ for MYG107 in comparison to the survival rate of PTA-5854 at about $5.1\times10^{-1}$.

An alcohol sensitivity test was performed in a similar fashion except that butanol was added to 1% (v/v). The butanol treatment resulted in a survival rate about less than $10^{-9}$ for MYG107 in comparison to the survival rate of PTA-5854 at about $5.6\times10^{-1}$.

A detergent sensitivity test was performed in a similar fashion except that SDS was added to 1% (w/v). The SDS treatment resulted in a survival rate about less than $10^{-9}$ for MYG107 in comparison to the survival rate of PTA-5854 at about $3.3\times10^{-1}$.

An oxidation sensitivity test was performed in a similar fashion except that hydrogen peroxide was added to 1% (w/v). The hydrogen peroxide treatment resulted in a survival rate about less than $10^{-9}$ for MYG107 in comparison to the survival rate of PTA-5854 at about $3.3\times10^{-1}$.

In a lysozyme sensitivity test, the wild-type PTA-5854 strain and MYG107 were grown in liquid LB medium at 37° C. for two days, and the cells were then dispensed into sterile microfuge tubes as 100 μl aliquots. Lysozyme was added to a concentration of 1 mg/ml and the cells were incubated at 37° C. for 60 minutes. The lysozyme-treated and untreated cells were plated onto LB-agar and incubated at 37° C. overnight to determine plating efficiency. The lysozyme treatment resulted in a survival rate about less than $10^{-9}$ for MYG107 in comparison to a survival rate of PTA-5854 at about $7.2\times10^{-1}$.

In a pressure sensitivity test, the wild-type PTA-5854 strain and MYG107 were grown in liquid LB medium at 37° C. for two days. A portion of the culture was pressure-treated (at 40,000 psi) in a French Press three times at room temperature. The survival rate for French pressuring was calculated (the plating efficiency of treated cells/the plating efficiency of untreated cells). The French pressuring treatment resulted in a survival rate about less than $10^{-9}$ for MYG107 in comparison to a survival rate of PTA-5854 at about $1.5\times10^{-1}$.

In a starvation sensitivity test, the wild-type PTA-5854 strain and MYG107 were grown in liquid LB medium at 37° C. for seven days. The survival rate for starvation was calculated (the plating efficiency at Day 7/the plating efficiency at Day 2). The starvation treatment resulted in a survival rate about less than $10^{-9}$ for MYG107 in comparison to a survival rate of PTA-5854 at about $3.3\times10^{-1}$.

In a dehydration sensitivity test, the wild-type PTA-5854 strain and MYG107 were grown in liquid LB medium at 37° C. for two days, and the cells were then dispensed into sterile microfuge tubes as 100 μl aliquots and subject to a speed-vacuum for 60 minutes at room temperature. The vacuum-dried cells (re-hydrated with 100 μl sterile distilled water) and untreated cells were plated onto LB-agar and incubated at 37° C. overnight to determine plating efficiency. The survival rate for vacuum-drying was calculated (the plating efficiency for treated cells/the plating efficiency of untreated cells). The vacuum-drying resulted in a survival rate about less than $10^{-9}$ for MYG107 in comparison to the survival rate of PTA-5854 at about $3.9\times10^{-1}$.

In another dehydration sensitivity test, the wild-type PTA-5854 strain and MYG107 cells were inoculated into growth media containing 10% and 20% soybean meal respectively. Cell growth was achieved for both strains in medium containing 10% soybean meal but not in the medium containing 20% soybean meal. Dilution of the 20% soybean meal cultures with sterile distilled water (1:1) restored growth for PTA-5854 but not MYG107, indicating that cells of a sporulation-deficient *B. texasporus* strain require a water content level of at least about 80% in the environment to sustain viability.

The characteristics of MYG107, MYG110 and MYG113 and the method of creating such strains, allow sporulation-deficient strains of *B. texasporus* to be used as an economically feasible DFM. In particular, the strains of the invention provide for the use of multiple inactivation methods that are incompatible with inactivation of wild-type *B. texasporus* cells (e.g., pasteurization and/or dehydration), which provides strains that may be used as an economically feasible DFM.

Inactivated *B. texasporus* cells were compared to purified peptides to demonstrate that the inactivated cells functioned equivalently to the purified peptides. BT peptides are produced by actively dividing *B. texasporus* cells, indicating that BT peptides are not "secondary metabolites" produced in response to starvation. In an LB culture, $10^6$ BT cells contain about 10 microgram of BT peptides. In other words, $10^{11}$ BT cells will contain about 1 gram of BT peptides.

The BT peptide concentration in inactivated *B. texasporus* cells was determined and an amount of inactivated cells equivalent to a desired concentration of purified peptide was used in the study. Newly hatched chicks were fed with diets with different concentrations of purified BT peptides or inactivated *B. texasporus* cells for two days. On Day 3, the chicks were inoculated with an invasive *Salmonella enterica* serovar *Enteritidis* (SE) strain. On Day 4, the chicks were sacrificed. The liver and spleen were harvested and homogenized. The presence or absence of the SE strain in the homogenate was determined. Birds receiving no BT peptide or cells were found to have an SE infection rate of 60%, Birds receiving 12 ppm of purified peptide or an amount of the inactivated cells equivalent to 12 ppm had SE infection rates of 28% and 52% for the purified peptide and 35% for the inactivated cells. Birds receiving 24 ppm or the equivalent amount of the inactivated cells had infection rates of 36% and 16% for purified peptide and 25% with the inactivated cells. Birds receiving 48 ppm or the equivalent amount of the inactivated cells had infection rates of 27% and 24% for the purified peptide and 10% for the inactivated cells.

Non-purified BT peptides in the inactivated cells displayed the same in vivo efficacy in preventing *Salmonella* organ invasion as purified proteins. Therefore, inactivated *B. texasporus* cells are equivalent to purified peptides.

Example 2

In order to assess the effect of veterinary-grade BT peptides (comprising inactivated *B. texasporus* cells which contain immunomodulatory BT cationic peptides) in preventing necrotic enteritis caused by an oral challenge of *Clostridium perfringens* (type A), necrotic enteritis lesions and/or mortality were obtained in challenge birds.

In Experiment 1, veterinary-grade BT at about 24 ppm and about 48 ppm delivered in feed reduced necrotic enteritis lesion scores from 2.3 to 0.6 and 0.5 respectively, mortality from 17% to 6% and 7%, respectively, and intestinal recovery of *C. perfringens* from 3.60 to 2.36 and 2.48 ($\log_{10}$ cfu/g) respectively ($p\leq0.05$).

In Experiment 2, veterinary-grade BT at about 24 ppm and about 48 ppm delivered in feed reduced necrotic enteritis lesion scores from 2.8 to 0.8 and 0.6 respectively, mortality from 21% to 5% and 1%, respectively, and intestinal recovery of *C. perfringens* from 3.12 to 1.88 and 1.31 ($\log_{10}$ cfu/g) respectively ($p\leq0.05$).

These results demonstrate that orally delivered inactivated *B. texasporus* cells are effective in preventing necrotic enteritis in broilers.

Results:

TABLE 3

Prevention necrotic enteritis in broiler chickens with oral delivery of inactivated *B. texasporus* cells

| Treatment[1] | Dosage | Lesion Score[2] | Mortality[3] | $Log_{10}$ cfu/g[4] |
|---|---|---|---|---|
| Experiment 1: | | | | |
| Control diet | NA | 2.3 | 17/100 (17%) | $3.60^A$ |
| Veterinary-grade BT | 24 ppm | 0.6 | 10/150* (6%) | $2.36^B$ |
| Veterinary-grade BT | 48 ppm | 0.5 | 11/150* (7%) | $2.48^B$ |
| Experiment 2: | | | | |
| Control diet | NA | 2.8 | 21/100 (21%) | $3.12^A$ |
| Veterinary-grade BT | 24 ppm | 0.8 | 5/100* (5%) | $1.88^B$ |
| Veterinary-grade BT | 48 ppm | 0.6 | 1/100* (1%) | $1.31^B$ |

[1]Treatment groups represented by the 24 and 48 ppm are BT concentrations administered from day 1.
[2]Lesion scores are represented by the mean of the treatment subset *n = 25) with mean square error.
[3]Mortality is represented by incidence data compared to the positive control (control diet) ($p < 0.05$).
[4]Log10 cfu/g is represented by the mean of the treatment subset (n = 10).
[A-B]Means within the same column with no common superscripts differ significantly ($p < 0.05$).

Materials and Methods:

On day of hatch, chicks were obtained from Sanderson Farms (Bryan) and randomly divided into experimental groups and placed into individual floor rearing pens on clean pine shavings. All animals received a commercial whole-wheat based broiler starter diet that met or exceeded NRC guidelines and water ad libitum. Birds fed either control diet, or diets containing either 24 ppm or 48 ppm of veterinary-grade BT peptides from day 1 through day 24.

Multiple isolates of *C. perfringens* (type A) obtained from active field cases in Virginia, North Carolina and Georgia was used in this investigation. The isolate was grown in thioglycollate medium. Sterile thioglycollate medium was used to inoculate the chickens; birds were challenged once a day for three days (days 17-19 post-hatch) by oral gavage (1.5 ml/challenge).

Each batch of *C. perfringens* produced for challenge was serially diluted and plated on SFP agar plates and then placed in the incubator at 37° C. for 24 hrs. The plates were then counted and recorded in order to determine the amount of *C. perfringens* given to the birds. To quantitative measure the recovery of *C. perfringens*, a section of the small intestine was removed; this piece of intestine was cranial to Meckel's diverticulum. Once the intestine was removed it was placed in a whirl pak bag with 10 ml of thioglycollate and stomached for 30 seconds. Then 0.5 ml was removed and place in an anaerobic thioglycollate and serially diluted and placed on SFP agar. The SFP agar was prepared as per label instructions. This media is an overlay media the initial layer was poured several days prior to the experiment and incubated to test for contamination. The second layer was applied the day of the necropsy in aerobic conditions, after the sample had been plated. The plates were then transported into the coy box, and the plates were incubated for 24 hrs and read the following day.

To evaluate gross lesions associated with NE, the jejunum and ileum of the small intestine were examined. Lesion scores were recorded using the following criteria:

0=No gross lesions, normal intestinal appearance.

1=Thin-walled or friable, gray appearance

2=Thin-walled, focal necrosis, gray appearance, small amounts of gas production.

3=Thin walled, sizable patches of necrosis, gas filled intestine, small flecks of blood.

4=Severe extensive necrosis, marked hemorrhage, large amounts of gas in intestine.

This study demonstrates the effectiveness of inactivated *B. texasporus* cells in priming the immune system of an animal prior to a bacterial challenge and that a primed immune system responds more rapidly or more effectively to such a challenge.

Example 3

Veterinary grade BT (inactivated *B. texasporus* cells) are actually non-antibiotic, although the cells carry the natural BT peptides that appear to have an antibiotic activity when measured with an in vitro assay. However, the in vitro assay is believed to produce an artificial result. BT does not act as an antibiotic in vivo, instead it is believed to enhance/prime the immune system of the animal, explaining why beneficial and commensal bacterial levels remain relatively unaffected but the levels of detrimental bacteria are reduced in animals treated with BT peptides or cells. This also explains why orally delivered veterinary grade BT (in inactivated cells) at 96 ppm had no impact in vivo on what appeared, using the in vitro assay, to be BT-sensitive beneficial and commensal gut bacteria (see Example 4).

Example 4

The aim of this experiment was to evaluate the safety of feeding veterinary grade BT (inactivated *Brevibacillus texasporus* cells which contain BT peptides, referred to as "BT peptide") at a high level of 96 ppm in broiler chickens with or without the stress of an *Eimeria maxima* challenge. The feeding trial was performed as two sequential separate trials.

Material and Methods:

Ross 508 type broiler chicks were hatched on two separate days approximately one month apart in a commercial hatchery. In both trials 66 cock chicks were transported to the chicken house. Chicks were weighted and caged in groups of four or five. At day 13 after arrival in the chicken hours the birds were moved to four rooms each with two pens, with each pen housing eight birds. One control group and one BT peptide group was present in each room. After the birds had been moved to the pens the *E. maxima* oocysts (tap water for control birds) were tube fed into the birds' crops.

Temperature and relative moisture were measured automatically 24 hours a day. During the first and second experimental day the temperature was over 30° C. and then was dropped down about 0.5° C. daily until it reached 20° C. Light programme was 24 h daily lights throughout the experiment.

TABLE 4

The amount of birds per treatment

| | Control | BT peptide |
|---|---|---|
| Trial 1 | 32 + 2 extra bird | 32 |
| Trial 2 | 32 + 2 extra bird | 32 |

The diets consisted of wheat, soybean meal, barley, rapeseed meal, rapeseed oil, vitamins, minerals and amino acids. The unmodified feed was obtained from Agrifood Research Finland MTT, Jokioinen. The feed was in mesh form and no coccidiostat or enzymes were added. Veterinary grade BT was added to the feed to the equivalent of a BT peptide concentration of 96 ppm. The treatment groups got the same diet throughout the experiment. The feed and water was offered ad libitum.

TABLE 5

Diet composition

| Composition of experimental feed | g/kg diet |
|---|---|
| Wheat | 549.8 |
| Barley | 40.00 |
| Soybean meal | 288.00 |
| Rapseed meal | 39.00 |
| Monocalcium phosphate | 39.00 |
| Ca | 19.00 |
| Salt | 14.00 |
| Limestone | 4.20 |
| Vit/Min | 2.00 |
| Methionine | 2.00 |
| Lysine | 1.60 |

TABLE 5-continued

| Diet composition | |
|---|---|
| Calculated chemical composition | g/kg diet |
| DM | 890.00 |
| Crude protein | 220.80 |
| Crude fat | 60.45 |
| Crude fiber | 31.31 |
| Ash | 59.44 |
| Ca | 10.11 |
| P | 8.32 |
| Digestible P | 4.79 |
| Na | 1.72 |
| Lys | 11.91 |
| Met | 4.82 |
| Cys | 3.87 |
| Thr | 8.24 |
| Calculated energy content | MJ/kg DM |
| ME | 12.20 |

Feed 1 = control feed
Feed 2 = control feed + veterinary grade BT at the equivalent of 0.096 g peptides per kg All the birds in three of the four rooms received *E. maxima* oocysts at day 13, while the fourth room was a control room for non-challenged birds. The dosage was approximately 25,000 sporulated oocysts per bird. The oocysts were tube-fed into the crop in a 2 ml of tap water. The *Eimeria* oocysts were purchased from the Veterinary Laboratories Agency, Surrey, United Kingdom. One room was without the challenge.

The birds were weighed at cage basis at arrival, 6, 13, 17, (18, and 19 in trial 2) and 20 days of age. The feed intake was measured at 6, 13 and 20 days of age. Feed intake was measured on a cage or pen basis. The condition of the birds was checked at least twice a day. The mortality rate and the weight of birds that died were recorded. Birds that were very ill or damaged birds were humanly euthanized. At the age of 20 days, chicks were killed by cervical dislocation and sampled for ileal and caecal digesta, yielding 32 digesta samples per treatment and trial.

Microbial Analysis of the Digesta Samples and Cell Lysis and Isolation of Chromosomal DNA The recovered bacterial DNA was analysed by quantitative PCR, allowing the quantity of different bacterial groups to be calculated. The following bacteria were analysed *Bifidobacterium* spp, *E. coli, Lactobacillus* spp. and the *C. perfringes* group cluster I. For the determination of DNA, triplicate samples were used, and the mean quantity of bacteria per gram fresh digesta weight was calculated.

The total bacterial cell counts in the digesta samples were determined by flow cytometry.

*Eimeria* lesion scoring was performed only for the first trial and unbiased expert identified the lesions. The identification of *Eimeria* lesions was made to the last part of the jejunum and whole ileum. The lesions are scored in a scale from 0-4 where 0 indicates a normal intestine and 4 indicates a seriously injured intestine.

The weight of bursas was measured from two birds from every pool. The bursas were weighted only for the second trial.

The total length of the small intestine (jejunum+ileum) was measured from every bird.

T-tests were calculated and used to measure the statistical differences between the treatments.

Figure 2:
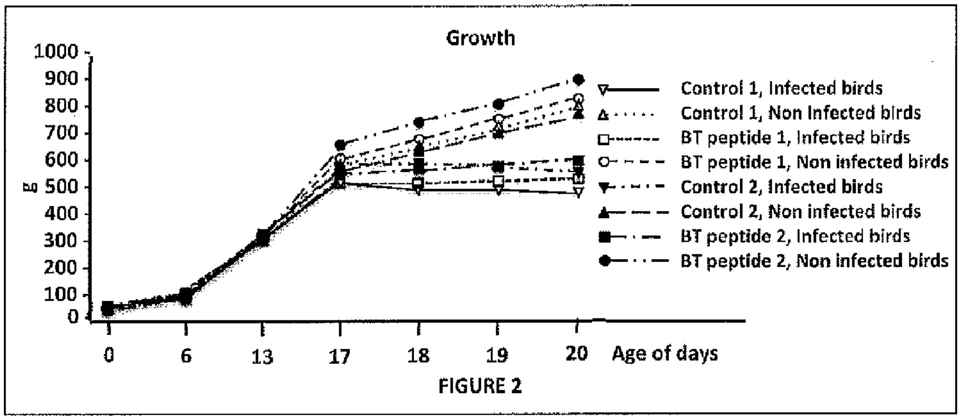
FIG. 2 shows the growth of birds during a first (1) and second (2) trial.
Figure 3:
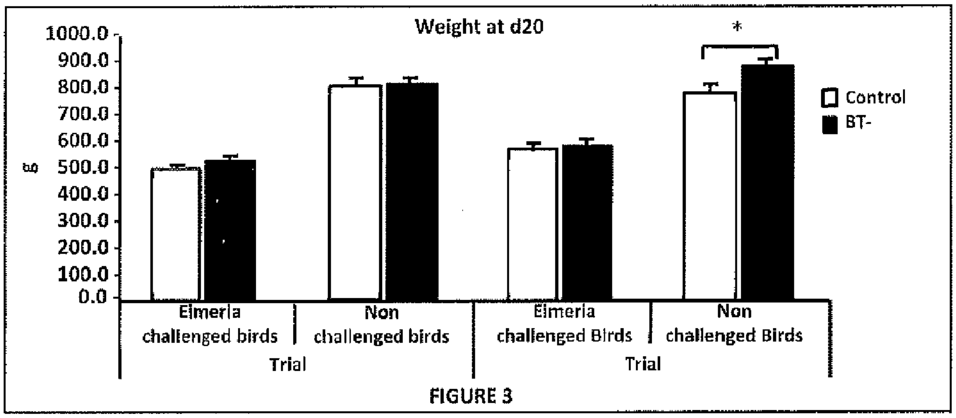
FIG. 3 shows the average weight of birds combined from both trials at day 20 (mean±SE). N=39-42 of challenged birds per treatment and N=16-19 of non-challenged birds per treatment. *$p\leq0.05$

Results:

The *Eimeria* challenge significantly decreased the growth of the control birds. However, the BT peptide-supplemented diet indicated somewhat increased growth of the birds, both in the non-challenged and *Eimeria*-challenged groups compared to the control group (FIG. 2). At day 20 the birds in BT peptide group appeared slightly heavier but no statistically significant difference could be identified (FIG. 3). If the weight of the non-challenged birds at day 20 was examined separately from the first and second trial, the weight of birds in the second trial was significantly (p=0.026) increased by the BT peptide supplemented diet when compared to the control group.

Figure 4:
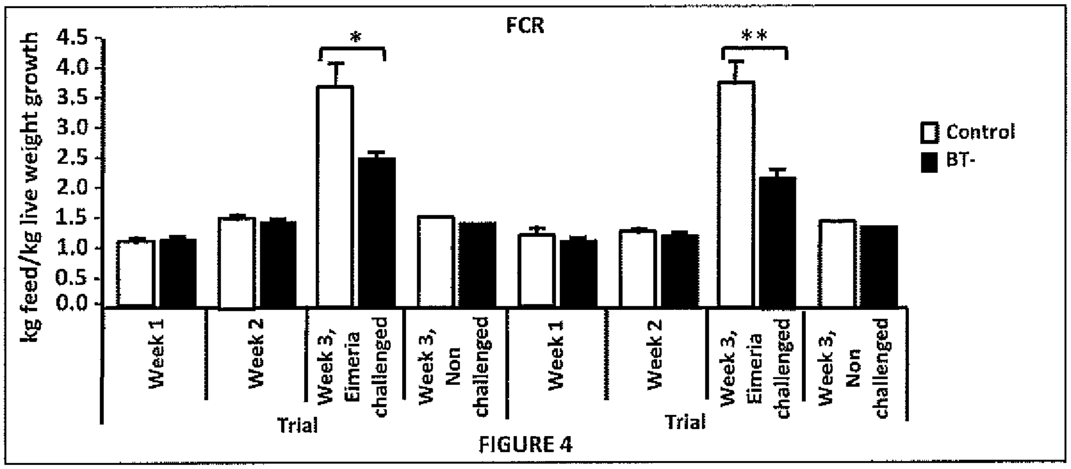
FIG. 4 shows the average feed conversion ratios from both trials as measured for the entire feeding treatment (mean±SE, N=3 pens/treatment/trial challenged birds, N=1 pens/treatment/trial non challenged birds) (1=trial 1, 2=trial 2). *$p\leq0.05$,  $p\leq0.01$

During the *Eimeria* challenge (between day 13 and 20 d) the feed conversion ratio (FCR) was improved in the BT peptide group when compared to the control group (p=0.02 for the first trail and p=0.006 for the second trial) (FIG. 4).

Figure 5:
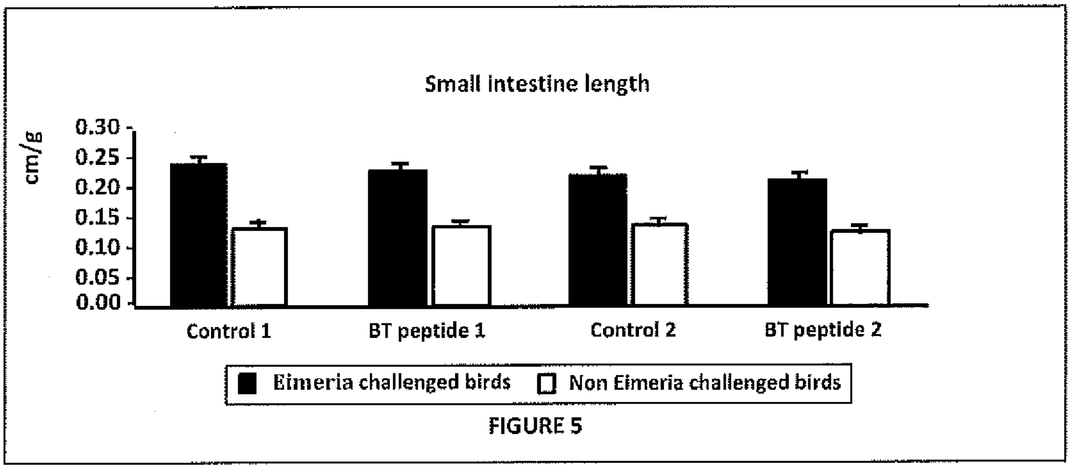
FIG. 5** shows the average of the length of the small intestine (mean±SE) in *Eimeria*-challenged birds (N=20-24) and for non-challenged birds (N=8) from both trials (1=trial 1, 2=trial 2).

The *Eimeria* challenge increased the length of small intestine as expected. The increased length of the small intestine may indicate compensatory growth due to the decreased nutrient absorption. However, there was no statistically significant difference in the average lengths of the small intestine between the treatments (FIG. 5).

Figure 6:
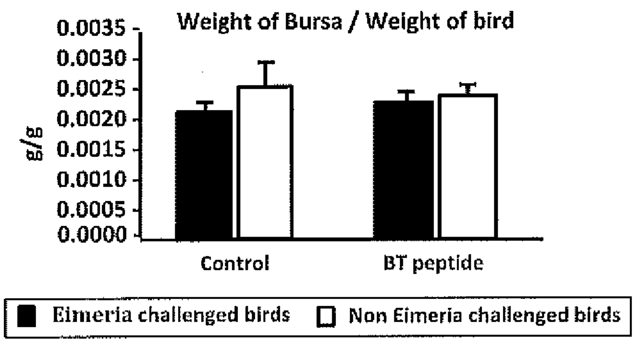
FIG. 6 shows the average ratio of the bursa weight to the bird weight (mean±SE) in the *Eimeria*-challenged (N=10-12) and non-challenged birds (N=4).

The bursa of Fabricius is an epithelial and lymphoid organ found only in birds. The bursa is the site of hematopoiesis, and is a specialized organ essential for the development of B cells. Bursa develops as a dorsal diverticulum of the proctadael region of the cloaca. For the second trial, the bursae were weighed and compared to the birds live weight. The proportion of the weight of the bursae when compared to the live weight of the birds appeared slightly bigger in the non-challenged birds than the *Eimeria*-challenged birds. No differences were noted between the BT peptide supplemented and the control group. However, the bursae of the non-challenged birds appeared somewhat bigger in the control group than in the BT peptide group (FIG. 6).

Figure 7:
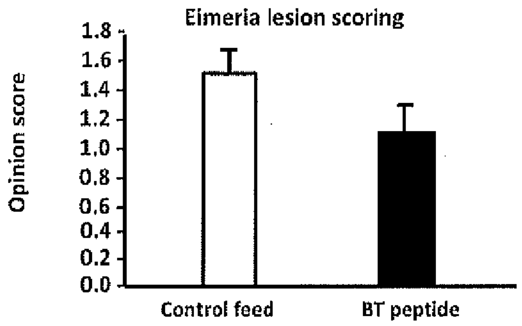
FIG. 7 shows the results of *Eimeria* lesion scoring (mean±SE) for the control (N=8) and in BT peptide (N=12) group. There was statistically significant difference between treatments (p=0.098).

The *E. maxima* mainly infect the middle region of the small intestine, the distal jejunum and proximal ileum. No high infection scores were detected probably because the peak of the infection was already surpassed, when the lesion scoring was preformed, at day seven day after the *E. maxima* inoculation. The average life cycle of *E. maxima* is between five to six days. The average score was lower in the BT peptide supplemented birds (p=0.098) as an indication of faster recovery or reduced inflammation (FIG. 7).

There was no mortality in unchallenged birds with either diet in both trials. The mortality of the *Eimeria*-challenged birds was relatively high. During first trial the mortality was the highest in control group and the lowest in the BT peptide group (p=0.011), while the situation was reversed during the second trial. When the mortality of both trials was combined, the over-all mortality appeared somewhat lower in the BT peptide group than in the control group, but the difference was not significant (Table 6). The reason for why the mortality rate was different between the treatments in trial 1 than trial 2 could be that in trial 2, very severely sick birds were promptly euthanized. In trial 1 none of the birds from the BT peptide group and three birds from the control feed group were sacrificed before the end of the trial. In trial 2 three birds from the BT peptide group and one bird form the control feed group were sacrificed before the end of the trial.

TABLE 6

| Mortality (%) | | | |
|---|---|---|---|
| Treatment | Trial 1 | Trial 2 | Mortality from both trials |
| Control | 23.5 | 11.8 | 17.6 |
| BT | 3.13 | 15.6 | 9.4 |

Figure 8:
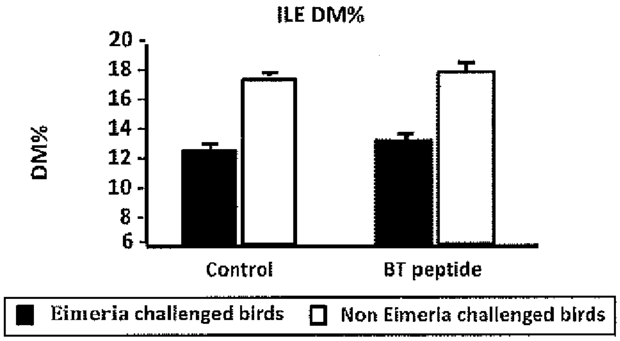
FIG. 8 shows the average percentage of dry matter of the ileum digesta (mean±SE) in challenged (N=5-6 pools per treatment) and from non-challenged birds (N=2 pools per treatment).

The percentage of digesta dry matter is an important background parameter, as it indicates the health of the gut and balance of the microbiota. The *Eimeria* challenge inflicted diarrhoea to the birds and decreased the dry mater content of the ileal and caecum digesta. These results suggest that the challenged birds had some problem with intestinal health and that the *Eimeria* challenge affects the balance of the intestinal microbiota. The effect of the BT peptide on the ileum dry matter of *Eimeria* challenged and non-challenged birds was not significant (FIG. 8).

Figure 9:
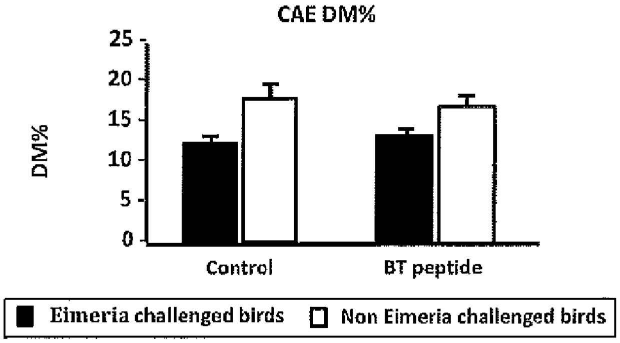
FIG. 9 shows the average percentage of dry mater of the caecal digesta (mean±SE) in challenged (N=4-6 pools per treatment) and in non-challenged birds (N=2 pools per treatment).

The digesta dry mater contents of the caeca were lower in the challenged than in the non-challenged birds. The dry mater of the caeca of *Eimeria*-challenged birds may have been slightly increased towards normal values by the BT peptide supplementation (FIG. 9).

Figure 10:
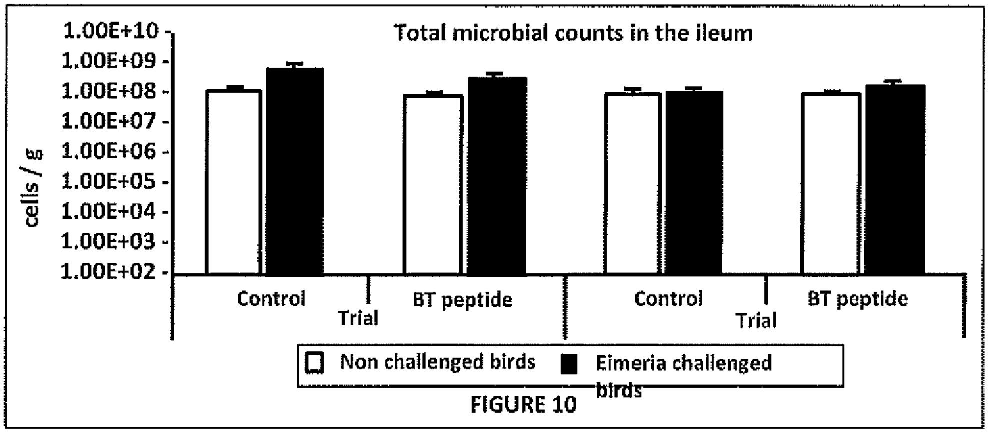
FIG. 10 shows the total microbial counts (mean±SE) in the ileum from challenged birds (N=5-6 pools per treatments) and from non-challenged birds (N=2 pools per treatment).
Figure 11:
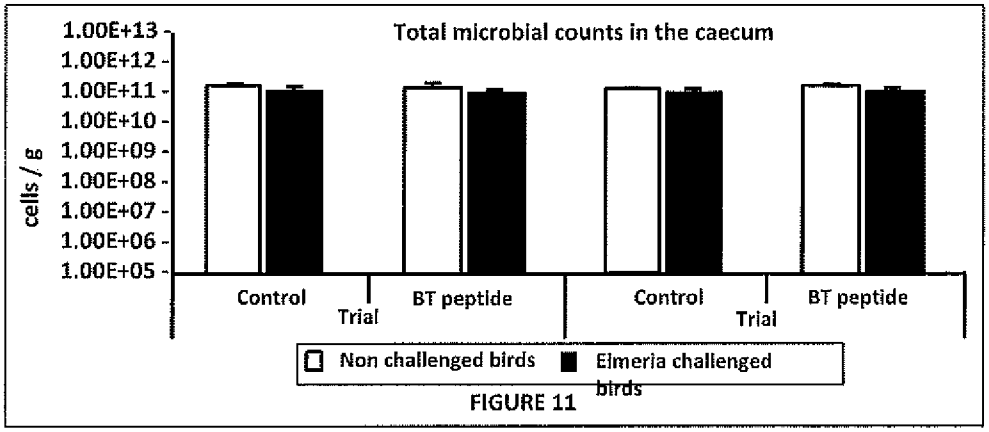
FIG. 11 shows the total microbial counts in the caecum (mean±SE) from challenged birds (N=5-6 pools per treatments) and, from non-challenged birds (N=2 pools per treatment).

The total number of microbes was higher in the caecum than ileum. The *Eimeria* challenge increased the total number of microbes in the ileum in both the control and the BT peptide supplemented groups. The numbers of microbes in the caecum decreased in both trials and both treatment groups due to the *Eimeria* challenge. No statistically significant difference between the two feed treatments in either trial could be detected (FIGS. 10 and 11).

Figure 12:
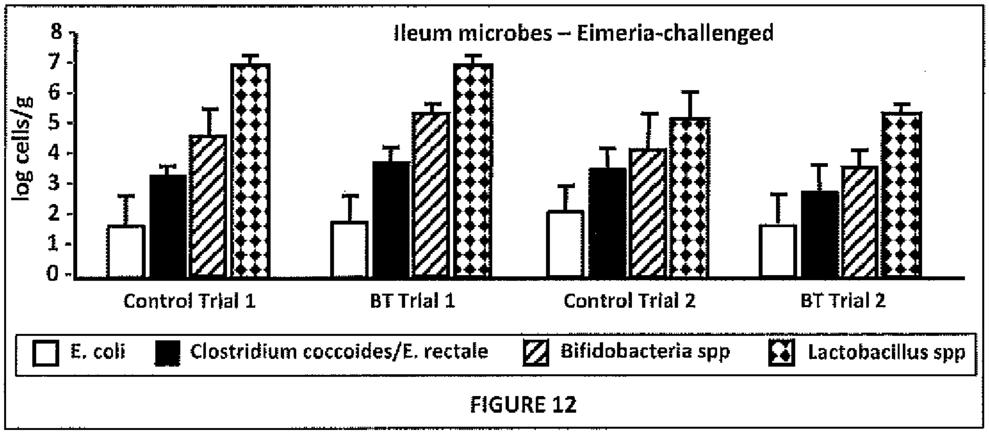
FIG. 12 shows the quantity of different microbes in ileum of *Eimeria*-challenged birds from both trials N=5-6 pools per treatment). P-value Control vs. BT, Trial 1=0.037.
Figure 13:
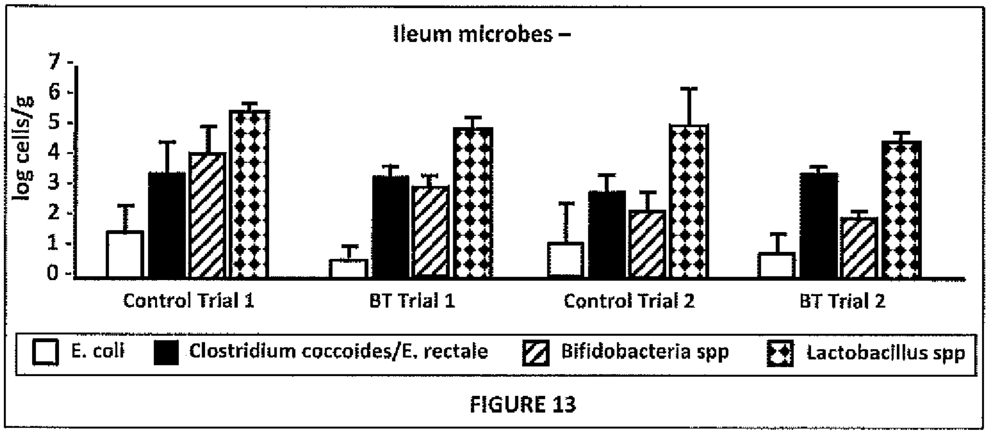
FIG. 13 shows the quantity of different microbes in ileum of unchallenged birds from both trials (N=2 pools per treatment). No significant differences between the groups.
Figure 14:
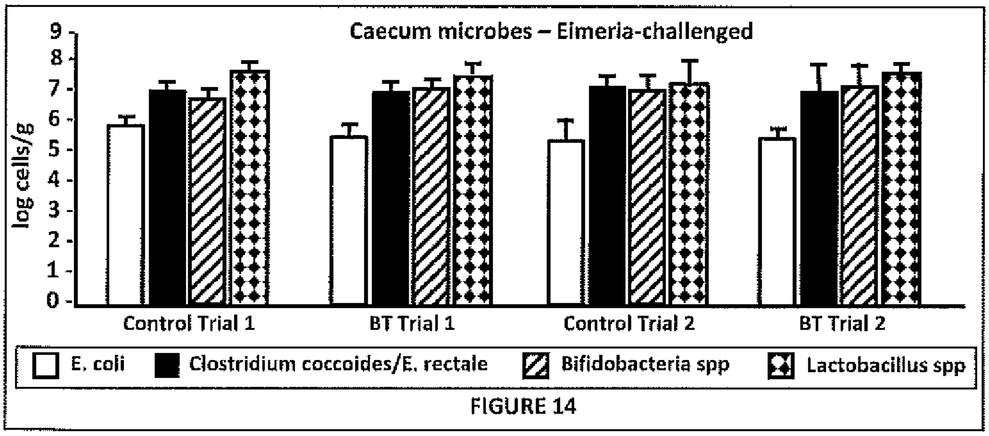
FIG. 14 shows the quantity of different microbes in caecum of *Eimeria*-challenged birds from both trials N=5-6 pools per treatment). No significant differences between the groups.
Figure 15:
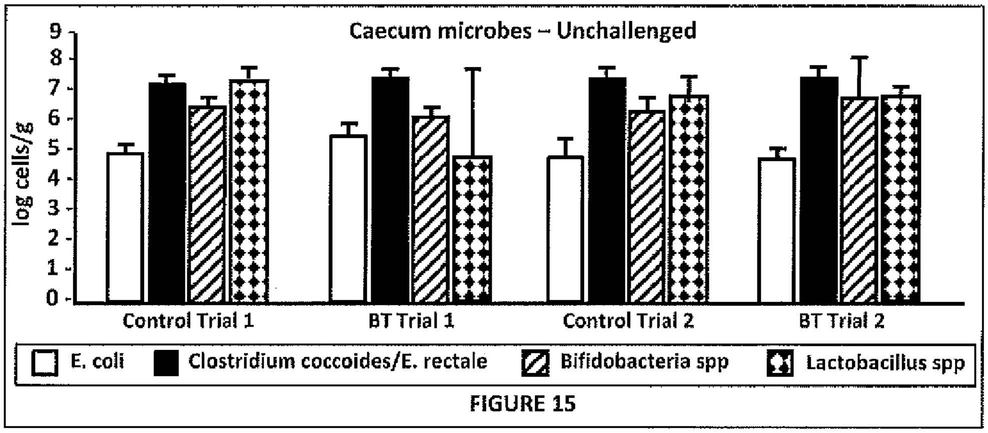
FIG. 15 shows the quantity of different microbes in caecum of unchallenged birds from both trials N=2 pools per treatment). No significant differences between the groups.

During these two trials, the *Eimeria* challenge tended to increase the numbers of *Lactobacillus* spp. and *Bifidobacteria* spp. in both the ileal and caecal digesta in both the control feed and the BT peptide supplemented groups. In trial 2, there was a statistically non-significant trend towards decreased bacterial levels in ileum in the BT peptide group, but in trial 1, there was an increase in the ileal levels of the *C. coccoides-E. rectale* group in the BT peptide group (FIG. 12). No differences in the unchallenged birds were observed (FIGS. 13 and 15). Bacterial content of the caecum was unaffected by the BT (FIGS. 14 and 15). No *Salmonella* spp. was detected in either trial. Taken together, the microbiota analyses suggest that at the current dose, BT peptide has little or no effect on native (non-pathogenic) bacterial populations, which indicates that the BT peptides are well tolerated by the treated animals and do not exhibit antibiotic effects.

This experiment demonstrates that no adverse effects on native or desired gut bacteria were detected in chickens supplemented with the BT peptide at 96 ppm. FCR was significantly improved in the BT peptide-supplemented group in *Eimeria*-challenged broiler chicken when compared to the control group (p=0.02 and p=0.006 for the first and second trial, respectively). The weight of birds in the second trial was significantly (p=0.026) improved by the BT peptide supplemented diet when compared to the control group. The mortality of the *Eimeria*-challenged broilers in the first trial was significantly (p=0.011) decreased by the BT peptide treatment when compared to the control group. Furthermore, supplementation of the feed by the BT peptide reduced the average lesion scores in the infected tissue (p=0.098).

Example 5

This study is to test the use of veterinary grade BT (inactivated *B. texasporus* cells) as a feed additive in swine for the effect on weight gain, *Salmonella* colonization and leukocyte function.

Materials and Methods

Experimental Design. At weaning (17-21 days of age), piglets were randomly placed in pens with heat lamps for additional warmth in groups of 5 individuals. Piglets were provided with water and an un-medicated Phase I diet ad libitum that meets the National Research Council (1994) guidelines. Body weights were recorded on Days 0, 3, 5, and 7 post-weaning. Pigs were placed into 4 experimental groups. Groups 1 and 2 each contained 5 pigs fed a control balanced unmedicated corn and soybean meal-based diet that contained 0 ppm or 12, ppm (repetition 1) or 24 ppm (repetitions 2, 3) BT peptides, respectively. Groups 3 and 4 were fed diets that contained 0 or 12 (or 24) ppm BT peptides, but pigs in these groups were challenged with *Salmonella typhimurium* (ST). Pigs were fed these diets throughout the experiments. The BT peptides were delivered in the form of inactivated *B. texasporus* cells as a premix.

*Salmonella enterica* serovar *Typhimurium* (ST). An isolate of *S. enterica* serovar *typhimurium* (ST) (National Veterinary Sciences Laboratory [NVSL]), Ames, Iowa (PT 24) was used and it is a strain that has been selected for resistance to carbenicillin and novobiocin (CN) and is maintained in TSB or tryptic soy agar at 4° C. Brilliant Green Agar (BGA), a selective culture media for *Salmonella*, was used to culture the resistant isolate in experimental studies and contained 100 μg/ml carbenicillin and 25 μg/ml novobiocin (i.e., BGA+CN) to inhibit growth of other bacteria. Inoculum for challenge was prepared from 18 to 24 h (TSB+CN cultures maintained at 41° C. and diluted in sterile PBS (pH 7.2). A stock solution ($1\times10^9$ cfu/ml) was prepared for challenge experiments.

At day 3 post-weaning, piglets in challenge groups were administered, by oral gavage, $10^7$ cfu ST. Five days post-challenge (7 days post-wean), pigs were euthanized and 1.0 g samples of cecal contents from each pig were collected aseptically. The cecal samples were serially diluted and spread-plated on brilliant green agar (BGA) plates. The plates were then incubated for 24 h at 37C and the number of cfu of ST per gram of cecal contents determined. In addition, tissues (liver, spleen, ileo-cecal lymph nodes, cecum and rectum will be cultured for the presence of ST using established methods. Suspect *Salmonella* colonies were confirmed by biochemical tests on triple sugar agar and lysine iron agar and further confirmed as ST by using *Salmonella* 0 antiserum. *Salmonella* colony plate counts are expressed as $\log_{10}$ *Salmonella* per gram of cecal contents.

Innate immune response in weaned pigs. Leukocytes were isolated using density gradient separation as previously described (KOGUT et al. 2010). Functional assays were performed to assess the capabilities of neutrophils isolated from pigs receiving the different treatments. Two methods of microbial killing used by neutrophils were investigated. Specifically, neutrophil degranulation, the release of bactericidal products from granules inside the neutrophil, and the oxidative burst, the production of bactericidal reactive oxygen species (ROS) were assayed. Briefly, the assays are described below.

Functional Assay.

Leukocyte oxidative burst was measured by oxidation of DCFH-DA to fluorescent DCF as described by (HE et al. 2003). Leukocytes are stimulated with phorbol A-myristate 13 acetate (PMA [2.0 μg/ml], Sigma) or RPMI 1640 media for 60 minutes prior to measurement. Cells were placed in 96-well plates and fluorescence measured using a GENios Plus Fluorescence Microplate Reader [(485/530 nm) Tecan US Inc., Research Triangle Park, N.C.

Statistical Analysis:

Statistical analysis was performed on data using SigmaStat® statistical software (Jandel Scientific, San Rafael, Calif., USA). Differences between the experimental groups will be determined using the Student T test. P≤0.05 was considered to be statistically significant.

Results.

From the data presented below, it appears pigs fed the BT cells had greater average daily gains in weight (ADG) than did pigs fed the control diet, even in the presence of a *Salmonella* infection (at 24 ppm) (Table 7).

TABLE 7

Average daily gain.

| Treatment | Average daily gain (lbs) Repetition 2 | Repetition 3 |
|---|---|---|
| Cont | 1.7 ± 0.3 | 0.04 ± 0.12 |
| Cont Pept 24 ppm | 4.2 ± 0.7 | 0.15 ± 0.06 |
| ST Cont | 3.2 ± 0.4 | 0.14 ± 0.09 |
| ST Pept 24 ppm | 4.6 ± 0.5 | 0.18 ± 0.06 |

Rep. 3, 24 ppm BT.
Values in pounds (lbs).
Data from weights collected on days 0, 3, 5, and 7 post weaning from individual pigs was pooled for each time point.
Data represents the average gain +/− standard deviation.

Some reductions in fecal shedding of ST were observed as shown in the rectal swab data (Table. 8). In Rep. 1, no difference was seen in fecal shedding at 12 ppm BT, except on Day 5. In Rep. 2, control and BT at 24 ppm were similar in ST shedding, except on Day 4, where the BT 24 ppm group had more pigs positive than the control group. In Rep. 3, the BT group at 24 ppm had less pigs shedding ST than did the control group on all days measured. In Rep. 3, pigs were followed for 7 days post-infection instead of 5 days, as in Rep. 1 and 2.

TABLE 8

Daily Rectal swab data

| | Number of pigs positive for ST | | | | | |
|---|---|---|---|---|---|---|
| | Rep 1 | | Rep 2 | | Rep 3 | |
| Days Post-infection | Control | BT 12 ppm | Control | BT 24 ppm | Control | BT 24 ppm |
| 1 | 2 | 3 | 4 | 3 | 5 | 2 |
| 2 | 5 | 5 | 4 | 4 | 3 | 1 |
| 3 | 5 | 5 | 3 | 4 | 4 | 2 |
| 4 | 4 | 5 | 2 | 5 | 4 | 1 |
| 5 | 3 | 1 | 1 | 1 | 5 | 2 |
| 6 | — | — | — | — | 5 | 1 |
| 7 | — | — | — | — | 4 | 3 |

Pigs fed the peptide had less *Salmonella* in the organs—lymph nodes, liver, spleen—as compared to the control pigs overall, but did not show reductions in the gut tissues—ileum (except rep 3), cecum, rectum. In Rep. 1, the BT group at 12 ppm had fewer pigs positive for ST in both the liver and the spleen, but recovery of ST was the same in the lymph nodes and the cecum and rectum (Table 9). In Rep. 2, the BT group had fewer pigs positive in all tissues, except the cecum. In Rep. 3, fewer pigs in the BT group were positive for ST in the lymph nodes, spleen, ileum, cecum, and rectum. Colonization data (CFUs) was indeterminate due to low recovery of ST (data not shown). It appears the peptide had some positive effects on *Salmonella* invasion and colonization in weaned pigs.

TABLE 9

*Salmonella* isolated from tissues

| | Number of pigs positive for ST | | | | | |
|---|---|---|---|---|---|---|
| | Rep 1 | | Rep 2 | | Rep 3 | |
| Tissue | Control | BT 12 ppm | Control | BT 24 ppm | Control | BT 24 ppm |
| Ileocecal lymph node | 3 | 3 | 5 | 1 | 4 | 2 |
| Liver | 3 | 1 | 5 | 1 | 2 | 2 |
| Spleen | 2 | 0 | 3 | 1 | 1 | 2 |
| Ileum | — | — | 5 | 4 | 4 | 0 |
| Cecum | 4 | 4 | 5 | 5 | 5 | 4 |
| Rectum | 5 | 5 | 5 | 4 | 4 | 3 |

Leukocytes from pigs fed the BT sporulation-deficient strain had a significantly higher oxidative burst response (Table 10) than did leukocytes from control pigs on days 3, 5, and 7 of being fed the BT peptide (P<0.05).

TABLE 10

Swine leukocyte oxidative burst activity.

| Treatment | Day 3 | Day 5 | Day 7 |
|---|---|---|---|
| Cont | 0.8 ± 0.1 | 1.2 ± 0.1 | 1.5 ± 0.3 |
| Pept | 1.5 ± 0.2 | 1.7 ± 0.3 | 2.2 ± 0.2 |
| Cont PMA | 23.0 ± 1.3 | 14.2 ± 1.0 | 30.4 ± 3.3 |
| Pept PMA | 39.2 ± 4.8 | 38.0 ± 3.5 | 40.5 ± 5.3 |

Pigs were fed respective diets throughout study period (24 ppm BT).
Pigs were bled on days 3, 5, and 7 post-weaning.
Data represents two repetitions, pooled from 10 pigs/group.
Data expressed as the mean +/− standard deviation.
RFU = reflective fluorescent units (in 1,000).

The data suggest that inactivated *B. texasporus* cells are an effective immunomodulator in swine with potential positive effects on weight gain and the carriage of *Salmonella* in the gut and tissues.

REFERENCES

All references, including publications, patents, patent applications and deposited strains, cited herein are hereby incorporated by reference to the same extent as if each reference were individually and specifically indicated to be incorporated by reference and were set forth in its entirety herein, including, but not limited to:

JIANG, Y. W., M. D. SIMS and D. P. CONWAY, 2005 The efficacy of TAMUS 2032 in preventing a natural outbreak of colibacillosis in broiler chickens in floor pens. Poult Sci 84: 1857-1859;

KOGUT, M. H., K. J. GENOVESE, H. HE, M. A. LI and Y. W. JIANG, 2007 The effects of the BT/TAMUS 2032 cationic peptides on innate immunity and susceptibility of young chickens to extraintestinal *Salmonella enterica* serovar *Enteritidis* infection. Int Immunopharmacol 7: 912-919;

WU, X., J. BALLARD and Y. W. JIANG, 2005 Structure and biosynthesis of the BT peptide antibiotic from *Brevibacillus texasporus*. Appl Environ Microbiol 71: 8519-8530;

KOGUT, M. H., H. HE, K. J. GENOVESE, and Y. W. JIANG, 2010 Feeding the BT Cationic Peptides to Chickens at Hatch Reduces Cecal Colonization by *Salmonella enterica* Serovar *Enteritidis* and Primes Innate Immune Cell Functional Activity. Foodborne Pathog Dis. 7(1): 23-30;

VIJAY-KUMAR, M., AITKEN, J., CARVALHO, F., CULLENDER, T., MWANGI, S., SRINIVASAN, S., SITARA-

MAN, S., KNIGHT, R., LEY, R., & GEWIRTZ, A. (2010). Metabolic Syndrome and Altered Gut Microbiota in Mice Lacking Toll-Like Receptor 5 *Science,* 328 (5975), 228-231;

HE, H., M. B. FARNELL, M. H. KOGUT, 2003 Inflammatory agonist stimulation and signal pathway of oxidative burst in neonatal chicken heterophils. Comparative. Biochemistry and Physiology A, 135, 177-184.

What is claimed is:

1. An isolated *Brevibacillus texasporus* strain selected from the group consisting of MYG107 (PTA-12309), MYG110 (PTA-12308), and MYG113 (PTA-12307).

2. An animal feed or drink comprising a strain of claim 1.

3. The animal feed or drink of claim 2, wherein at least $1.0\times10^{10}$ cells of the strain are inactivated per 1000 kg of said animal feed or drink.

4. The animal feed or drink of claim 2, wherein the amount of the strain is an amount in said animal feed or drink that is sufficient to increase feed conversion or the growth rate in an animal.

5. The animal feed or drink of claim 2, wherein said feed or drink comprises one of water, corn meal, cereal, soybean meal, isolated soybean protein, isolated soybean oil, isolated soybean fat, skimmed milk, fish meal, meat meal, bone meal, blood meal, blood plasma protein, whey, rice bran, wheat bran and combinations thereof.

6. The isolated *B. texasporus* strain of claim 1, wherein the strain is MYG107 (PTA-12309).

7. An animal feed or drink comprising an effective amount of the strain of claim 6.

8. The animal feed or drink of claim 7, wherein at least $1.0\times10^{10}$ cells of the strain are inactivated per 1000 kg of said animal feed or drink.

9. The animal feed or drink of claim 7, wherein the effective amount of the strain is an amount in said animal feed or drink that is sufficient to increase feed conversion or the growth rate in an animal.

10. The animal feed or drink of claim 7, wherein said feed or drink comprises one of water, corn meal, cereal, soybean meal, isolated soybean protein, isolated soybean oil, isolated soybean fat, skimmed milk, fish meal, meat meal, bone meal, blood meal, blood plasma protein, whey, rice bran, wheat bran or combinations thereof.

11. The isolated *B. texasporus* strain of claim 1, wherein said strain is sporulation deficient.

12. A method of inactivating an isolated *B. texasporus* strain, the method comprising subjecting a culture of cells of a *B. texasporus* strain to a stress sufficient to inactivate vegetative cells but insufficient to inactivate a) *Brevibacillus texasporus* (BT) peptides and b) a majority of spores present in the culture; wherein said *B. texasporus* strain is selected from MYG107 (PTA-12309), MYG110 (PTA-12308) and MYG113 (PTA-12307).

13. The method of claim 12, wherein the stress is selected from the group consisting of starvation, temperature shock, dehydration, pH changes, alcohol exposure, treatment with a detergent, pressure treatment, enzymatic disruption, mechanical force and combinations thereof.

14. The method of claim 12, wherein the stress is selected from the group consisting of heating the cells to at least 50° C. for at least 5 minutes, freezing the cells in the absence of a cryoprotectant, dehydrating the cells to a water content of less than 80%, adding a detergent, spray drying the cells, applying a mechanical force and combinations thereof.

15. An inactivated *B. texasporus* strain produced by the method of claim 12.

16. An animal feed or drink comprising an effective amount of an isolated *B. texasporus* strain and at least one feed or drink compound or composition selected from the group consisting of water, corn meal, cereal, soybean meal, isolated soybean protein, isolated soybean oil, isolated soybean fat, skimmed milk, fish meal, meat meal, bone meal, blood meal, blood plasma protein, whey, rice bran, wheat bran and combinations thereof; wherein said *B. texasporus* strain is selected from MYG107 (PTA-12309), MYG110 (PTA-12308), MYG113 (PTA-12307) and inactivated strains thereof.

17. The animal feed or drink of claim 16, wherein at least $1.0\times10^{10}$ cells of the strain are inactivated per 1000 kg of said animal feed or drink.

18. The animal feed or drink of claim 16, wherein the effective amount of the isolated *B. texasporus* strain is an amount that is sufficient to increase feed conversion or the growth rate in an animal.

19. A preparation comprising the isolated *B. texasporus* strain of claim 1, wherein the preparation has a water content of less than 50%.

20. A method of feeding an animal, the method comprising administering, to an animal, the isolated, inactivated *B. texasporus* strain of claim 15; thereby feeding the animal.

21. A method of feeding an animal, the method comprising administering, to an animal, the animal feed or drink of claim 17; thereby feeding the animal.

22. The method of claim 20, wherein the animal is a chicken, turkey, duck, pig, cow, or farmed fish.

23. The method of claim 21, wherein the animal is a chicken, turkey, duck, pig, cow, or farmed fish.

* * * * *